United States Patent [19]

Bodenheimer et al.

[11] Patent Number: 4,806,013
[45] Date of Patent: Feb. 21, 1989

[54] REFRACTOMETER FOR FLUIDS

[75] Inventors: Joseph S. Bodenheimer, Jerusalem; Itzhak Klein, Petach Tikva; Yehuda L. Levi, Jerusalem, all of Israel

[73] Assignee: Jerusalem College of Technology, Jerusalem, Israel

[21] Appl. No.: 918,047

[22] Filed: Oct. 14, 1986

Related U.S. Application Data

[63] Continuation-in-part of Ser. No. 568,497, Jan. 5, 1984.

[51] Int. Cl.$^4$ ............................................. G01N 21/14
[52] U.S. Cl. ..................................................... 356/133
[58] Field of Search ............... 356/128, 130, 132, 133, 356/134, 135, 136; 250/576

[56] References Cited

U.S. PATENT DOCUMENTS

| | | | |
|---|---|---|---|
| 3,282,149 | 11/1966 | Shaw et al. | 356/133 |
| 3,311,014 | 3/1967 | Witt et al. | 356/133 |
| 3,513,319 | 5/1970 | Broerman | 250/576 |
| 4,225,245 | 9/1980 | Roiret et al. | 250/205 |
| 4,306,805 | 12/1981 | Arrington | 356/133 |

FOREIGN PATENT DOCUMENTS 90243  7/1981  Japan .................................. 356/133

Primary Examiner—Richard A. Rosenberger
Attorney, Agent, or Firm—Amster, Rothstein & Ebenstein

[57] ABSTRACT

There is provided an apparatus for measuring the refractive index of fluids. The apparatus comprises a substantially U-shaped sensor rod made of a transparent material and is submersible in the fluid. The bent portion of the sensor rod has a diameter of curvature at least two times larger than the diameter of the sensor rod, and chosen so as to optimize sensitivity for a given range of indices. The two ends of the U-shaped sensor rod are connectable to a housing and a light source inside the housing has optical access to the face of one of the sensor-rod ends. A light detector means also disposed inside the housing has optical access to the face of the other one of the sensor rod ends.

8 Claims, 3 Drawing Sheets

REFRACTOMETER FOR FLUIDS

This is a continuation-in-part of application Ser. No. 568,497 filed on Jan. 5, 1984.

The present invention relates to optical measurements and more specifically to the continuous measurement of the refractive index (R.I) of fluids by means of light flux transmitted through an optical light guide immersed in the fluid.

The use of refractive index as an indicator for salinity, degree Brix solvent concentration, specific gravity or other characteristics of a fluid is well known, and is embodied in commercial instruments commonly known as refractometers, most of which use the critical-angle method for determination of R.I.

Some modifications of this method use multiple reflection in a glass rod, e.g., the devices described in U.S. Pat. No. 2,569,127 (Eltenton), 3,311,014 (Witt), 3,513,319 (Broerman). 3,282,149 (Shaw), in the European patent application No. 0027099 (Harmer). in the Japanese Patent JP No. 56-90243 (Yamazaki), and in the DDR Patent DD No. 147877 (Stoll et al).

The feature common to these devices is a transparent optical rod (or a Plurality thereof) which acts as a light guide when immersed in a fluid of lower R.I. than its own. Light impinging on one end of a transparent rod is trapped due to the phenomenon of total internal reflection (T.I.R.) and escapes via the other end, or via the same end, after multiple reflections within the rod. Since this is the effect used in fiber optics, these devices have been called fiber optic refractometers although usually a rod rather than a fiber, is used.

The amount of light traversing the rod in the above-mentioned manner depends, among other factors, upon the R.I. of the fluid in which the rod is immersed. Conversion of the light signal into an electrical signal by means of a photodetector enables continuous measurement of the refractive index, and thereby of the required characteristic property of the fluid. It must be stressed that T.I.R. trapping occurs only if the R.I. of the rod is greater than that of the liquid.

Several of the above-mentioned instruments, e.g.. U.S. Pat. Nos. 3,513,319 and 2,569,127 impose special conditions upon the sample chamber containing the rod and the fluid. Thus, the characteristics of the sampled region may differ from those of the bulk fluid. This is especially true for temperature-dependent characteristics, since the R.I. is a function of temperature. In those devices in which the rod does extend into the bulk of the fluid (e.g. Witt), one has to avoid penetration of the fluid into the measurement chamber containing light source, photodetector and other components, by means of a leak-tight seal such as O-rings or adhesives. Such seals result in optical contact between the rod and the sealant, due to which much of the light trapped in the rod will escape at the contact regions, thus reducing the sensitivity of the device. In some cases the device may be largely insensitive to fluids with an R.I. smaller than that of the adhesive.

Furthermore, since the significance of the relative bend radius D, i.e., the ratio between bend radius and rod radius has not previously been realized Prior art has by and large taught away from simple U shaped devices. This is evident from Harmer stating on page 3, line 12: "...these devices have the major drawback of having a very low sensitivity, so that their use as refractometers is quite limited (because of their inability to detect slight variations of the refractive index of the liquid to be tested)...". Similarly Broerman, in column 1 line 45 states: "However, a refractometer of this type does not possess the sensitivity required in many applications...".

Wherever preferred dimensions are mentioned, the relative bend radius has been chosen too small for good sensitivity and in all cases appears to be less than 10. Shaw, in column 3, line 65 states similarly: "Good results can be obtained with a rod about 9 mm in diameter and in which the loop is such that the ends 13 are about 7 cm apart. The shaping is not critical". Harmer, on page 5, lines 30-37 further states: "The radius of curvature R of the different curved portions will advantageously be chosen small in relation to the transverse dimensions of the light guide . . . so that the ratio R/r lies between about 3 and 5". In Stoll et al, the ratio is evidently less than 4:1.

In the Broerman refractometer, although each individual fiber has a large relative bend radius, these fibers cannot be considered as separate rods, because of unavoidable light leakage between the fibers in the active zone of which the cladding has been removed (column 1, lines 65-67 and column 3, lines 6-9). It is also significant that Broerman teaches away from a single sensor rod (column 1, lines 45-48). Indeed an individual fiber of the type preferred by Broerman (column 2, lines 65-69) would be flexible, and therefore not suitable for refractometry in liquid flows. The fluctuations that tend to occur in industrial liquid flows would cause changes in shape of the fiber that in turn would cause unwarranted variations ("noise") in the output of the detector. Therefore the Broerman patent cannot be considered to anticipate an essentially rigid U-shaped rod with a relative bend radius of 10 or greater. The non-rigid nature of the Broerman bundle is further indicated in column 3, lines 10-18, where a compressive force is used to separate individual fibers. The Broerman refractometer is further differentiated from the present invention in that its utility is restricted to a specially shaped sample chamber, wherein the fiber bundle occupies a significant fraction of the volume, as evident in FIGS. 2, 3 and 5. If the vessel were much larger, flexure of the fibers would strongly reduce the signal to noise ratio.

Arrington (U.S. Pat. No. 4,306,805) is essentially a modification of the classical Abbe refractometer, using a single reflection from a curved surface in contact with the fluid, with restrictions imposed upon the angles of incidence of the impinging light. Haumersen (DE No. 2642891) also uses a single reflection from a curved surface.

It is one of the objectives of the present invention to overcome the limitations and drawbacks of the prior art refractometers and to provide an apparatus for the continuous measuring and recording of the refractive index of a fluid which apparatus is highly sensitive over a relatively wide range determined by the geometry of a light-guide sensor.

This the present invention achieves by providing an apparatus for measuring the refractive index of fluids, comprising a substantially U-shaped sensor rod made of a transparent material and being submersible in said fluid the bent portion of which sensor rod has a diameter of curvature at least ten times larger than the diameter of said sensor rod, a housing to which are connectable the two ends of said U shaped sensor rod, a light source inside said housing, which light source has optical access to the face of one of said sensor-rod ends, and at least one first light detector means inside said housing, which light detector means has optical access to the face of the other one of said sensor rod ends.

It should be emphasized that the curvature of the sensor rod serves a dual function. It not only permits the rod to be immersed with both ends above the liquid, but it plays an essential role in the sensor function, as well. Since this fact is intimately related to the novelty aspect of the present invention some detailed explanations shall be given here.

The light rays entering the rod are generally distributed over a solid cone coaxial with the rod. Only the rays in the outer shell of that cone are affected by the R.I. of the liquid, these rays may be called "active". In a straight rod, rays do not change their angle relative to the cone axis and, therefore, active rays remain active and inactive ones never become active. Under these conditions, a fiber may lose all its active rays on passing, for instance, a feed-through, where it makes contact with a higher-index medium. Such a fiber will, then, no longer be functional.

The bending of the fiber changes this situation. Now, each reflection changes the angle the ray makes with the axis, moving rays from the shell into the core and vice versa, so that a ray-cone that has lost all its active rays will have them replenished as it is reflected repeatedly on its path through the bent fiber. On the other hand if the bend radius is too short, most of the rays—including the potentially active core rays—will be quickly lost and small changes in refractive index will not have much effect: sensitivity will drop rapidly. Thus the fiber bend radius plays a crucial role and can be used to optimize operation for certain index values.

The following empirical formula gives the minimum relative bend radius D(=bend radius/rod radius) for various values of relative index, N(=liquid R.I./rod R.I.)

$$D = A/(1-N)$$

where A is a constant depending on the required sensitivity, S, defined as the ratio of transmittance change to index change. If S=3, then A=1.6, and for S=1.5 (low sensitivity) A=0.8. Since most refractometers measure from n=1.33, index ratios lower than N=0.85 are not practical for most rod materials. Therefore, a relative bend radius of at least 10 is necessary for good sensitivity. It follows that the relative bend radius is a crucial design factor in the fiber optic refractometer, controlling both its sensitivity and operating range.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard no attempt is made to show structural details of the invention in more detail than is necessary for a fundamental understanding of the invention, the description taken with the drawings making apparent to those skilled in the art how the several forms of the invention may be embodied in practice.

Figure 1:
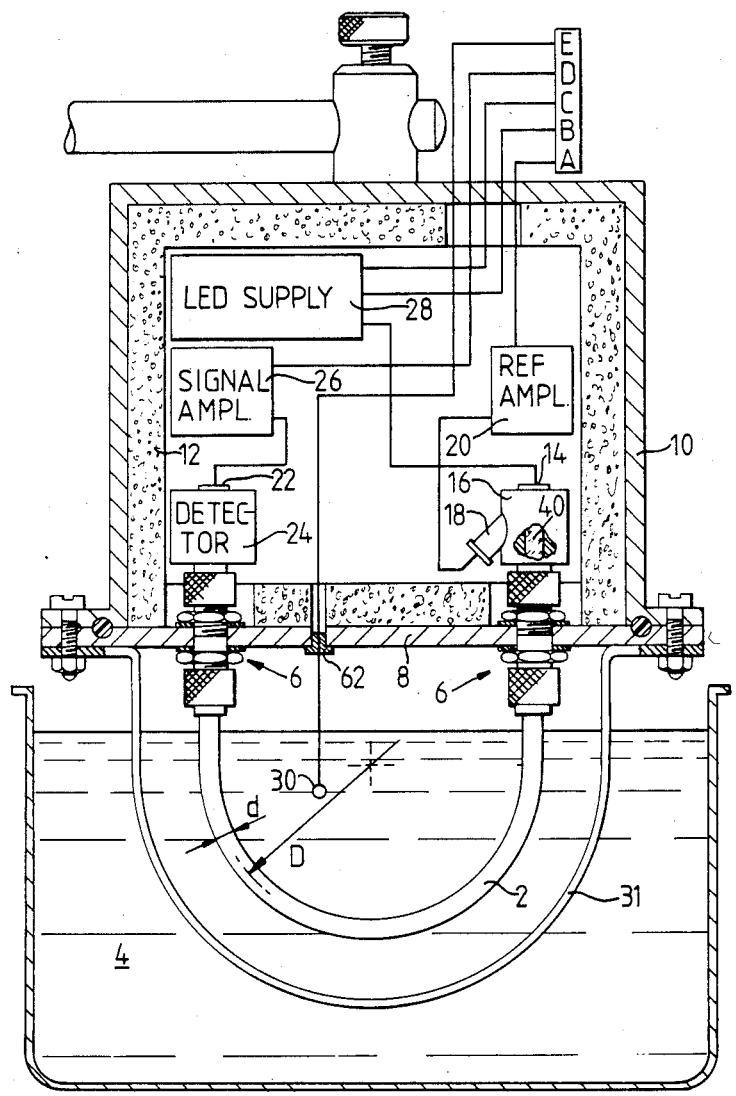
FIG. 1 is a partly schematic representation, in partial cross section, of a preferred embodiment of the refractometer according to the invention.

Referring now to the drawings, there is seen in FIG. 1 a substantially U-shaped rod 2 made of a transparent material such as glass. This rod serves as sensor and during measurement, is submerged in the liquid 4, the R.I. of which is to be measured. It has been found that in order to obtain good sensitivity, the bent portion of the sensor rod 2 must have a relative bend radius properly matched to the operating range of R.I. In order to cover most liquids of interest, the relative bend radius should be 10 or more, but advantageously not more than 200 in order not to restrict sensitivity to a very narrow range of indices close to the index of the rod itself. Sensitivity may be optimized with regard to a given range of R.I. from $n_{min}$ to $n_{max}$, by choosing the rod R.I. greater than $n_{max}$, and the minimum relative bend radius D according to the empirical formula:

$$D = A/(1-N_{min})$$

where $N_{min} = n_{min}/($rod R.I.$)$, and A equals 1.6 for a (high) sensitivity of 3.

Via fittings 6, shown in greater detail in FIG. 2 and described further below, the straight, parallel end portions of the U-shaped bar 2 are introduced into the bottom plate 8 of a hermetically sealable housing 10 provided with a thermally insulating internal lining 12 and accommodating the following components:

An input-light source in the form of a light-emitting diode (LED) 14 which is electronically pulsed to permit the filtering-out of ambient light. The LED used produces a quasi-monochromatic light of a wavelength of, e.g., 5850A, thus mnimizing index dispersion effects. (It should be noted that the R.I. is also a function of wavelength). LED's are furthermore known for their low power consumption and compact size which, as will be shown further below, also facilitates optical coupling to the sensor rod 2.

The LED 14 is mounted in a socket 16 which also accommodates a reference photodetector 18 that serves to monitor the input light flux provided by the LED. The signal produced by the photodetector 18 is led via a reference signal amplifier 20 to the terminal A.

Light from the LED is "piped" through the sensor rod 2. Depending on the respective angles of incidence at the rod walls, part of the light rays issuing from the LED are totally internally reflected and, disregarding some absorption losses, reach the other end of the rod largely undiminished. Depending on the difference between the respective R.I.'s of the rod material and the medium surrounding the rod 2, another part of the light flux is refracted out of the rod 2 and into the liquid 4. To establish this "lost" fraction of the flux and, thereby, in conjunction with the reference signal and a calibration curve, the R.I. of the liquid 4, there is further provided in the housing 10:

An output-light detector, in the form of a photodetector 22 mounted in a socket 24. The output signal of this detector is led via an output signal amplifier 26 to the terminal D.

Also accommodated in the housing 10 is a power supply unit 28 for the LED 14. This unit may by itself be a pulser or may be connected via terminal C to an external pulser, and via terminal B, to an external power supply.

Since, as already mentioned, the R.I. is also a function of temperature, the temperatures of both liquid 4 and rod 2 (which, due to the small thermal capacity of the rod are always substantially equal) must be continuously monitored. This is effected by a thermocouple, the hot junction 30 of which is immersed in the liquid 4 and is connectable to an external cold junction and digital voltmeter at terminal E.

A guard strip 31 protects the physical integrity of the sensor rod 2.

Figure 2:
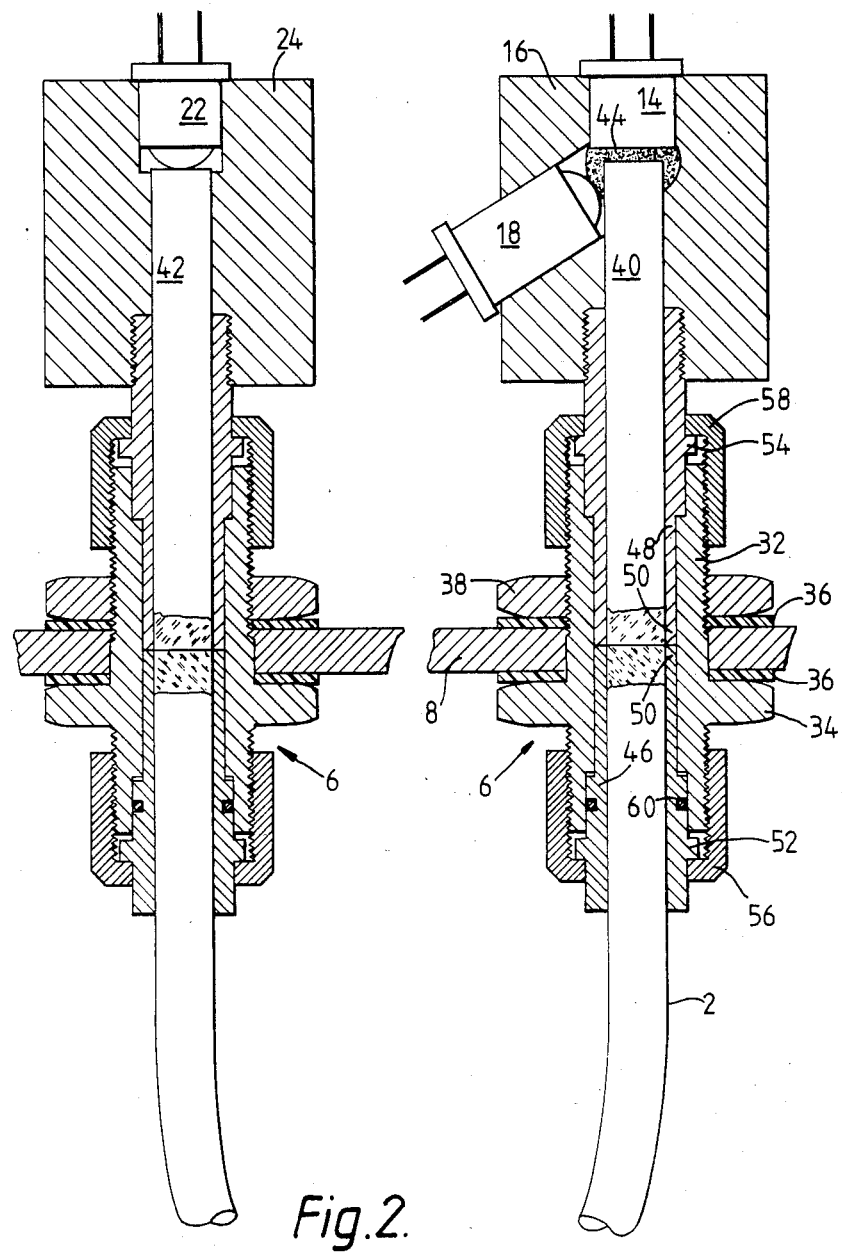
FIG. 2 is a greatly enlarged view, in cross section of the fittings and optical components of the embodiment of FIG. 1.

The fittings 6 and the associated components are shown greatly enlarged in FIG. 2, the right-hand part of which represents the "input" side and the left-hand part, the "output" side of the device. It is immediately seen that the parallel end portions of the U-shaped sensor rod 2 are not led right up to the LED 14 and the photodetector 22, respectively, but end at a much lower point, in a plane that, in the particular embodiment passes somewhere through the bottom plate 8. From there to the LED 14 and the detector 22, the light flux is guided through coupling rods 40 and 42 respectively. Intimate coupling between the LED 14 and the upper face of the input coupling rod 40 is established by grinding off the usually convex tip of the LED and cementing the top face of the coupling rod 40 to the flat surface thus obtained using a transparent epoxy cement 44. Optical coupling between the lower faces of the coupling rods 40 and 42 and the respective upper faces of the sensor rod 2 is effected by carefully pressing these faces one against the other after introducing a drop of a suitable oil. The provision of this contact force is in fact one of the tasks of the fittings 6.

The basic element of the two identical fittings 6 is seen to be a metal sleeve 32 having two externally threaded ends and a collar 34 which as can be seen in FIG. 1, is advantageously given a hexagonal shape. This sleeve 32 is inserted into appropriately dimensioned and spaced holes in the bottom plate 8 and, sealing washers 36 having been interposed as shown in FIG. 2, is clamped tight. Into the sleeves 32 fit slidingly lower ferrules 46 and upper ferrules 48, into which ferrules are cemented the straight end portions of the sensor rod 2 and the lower portions of the coupling rods 40, 42, respectively, the faces of the rods—coupling as well as sensor—being substantially flush with the respective ferrule rims 50. At a distance from these rims 50 the ferrules 46, 48 are provided with collars 52 and 54, respectively, which are engageable by union nuts 56 and 58, respectively, that match the threaded ends of the sleeves 32. By tightening these union nuts 56, 58, the sensor rod 2 and the coupling rods 40. 42 are Pressed against one another, as clearly seen in FIG. 2. Conversely, by unscrewing the two lower union nuts 56, the sensor rod 2 is easily withdrawn from the sleeves 32 for cleaning or replacement. An O-ring 60 in the lower, heavier portion of the ferrule 46 seals off any liquid access into the interior of the housing 10, which is of importance in cases where the entire device has to be submerged and not only the sensor rod 2, for instance when monitoring salinity gradients in solar ponds. In such cases, the wiring terminal A-E and the lead through 62 of the thermocouple 30 (FIG. 1) must obviously also be liquid-tight.

The respective arrangements of the LED 14, the reference photodetector 18 and the output photodetector as seen in FIG. 2 are self-explanatory. However, while the function of the reference detector 18 in R.I. determinations has been explained earlier, it should be noted that in some applications, e.g., process control the absolute value of the R.I. is of lesser interest than the constancy thereof, in which case the task of the reference detector 18 is reduced to monitoring the constancy of the input light flux and, in case of fluctuations, to actuate electronic compensation means. In prior art devices, this problem could only be solved by much more complex differential-refractometer arrangements.

Figure 3:
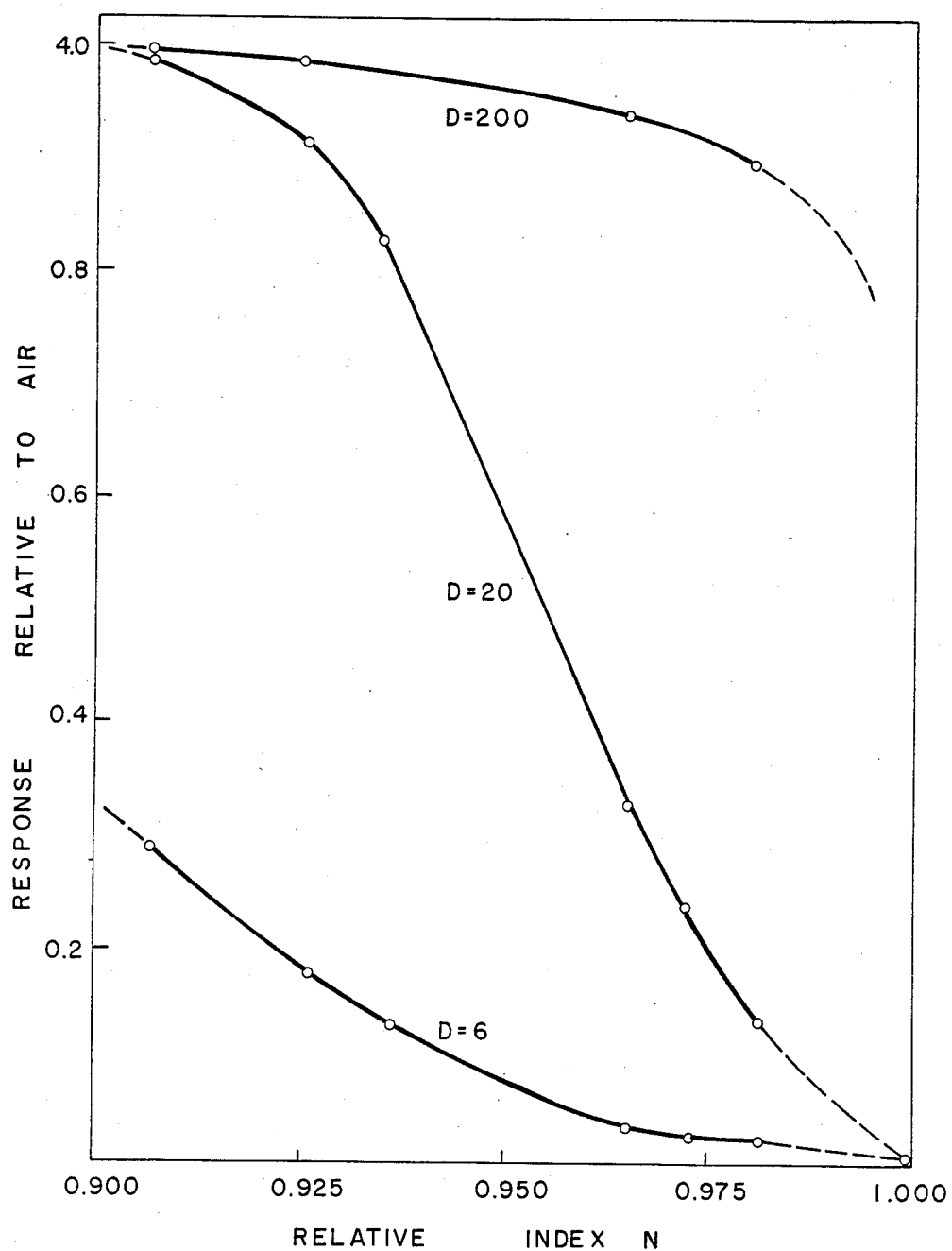
FIG. 3 is a graph showing the response of three U-shaped devices such as shown in FIG. 1, each having a different relative bend radius, the slope of the curve representing the relative sensitivity.

The empirical formula connecting the bend radius to the index is based on extensive ray tracing computations, using more than $10^6$ skew rays. FIG. 3 shows experimental evidence obtained to support these results. Pyrex glass rods were bent to a U shape and used in a configuration similar to that shown in FIG. 1. The photodetector signal response relative to the response obtained with the rod in air is plotted as function of the refractive index of the liquid relative to the rod index (n=1.470). The three curves correspond to relative bend radii of 200, 20 and 6 respectively. The slope of the curves is proportional to the sensitivity of the device. Taking into account experimental limitations and non-uniformities, these results confirm the computer results, and show the effect of the bend radius in determining the region of high sensitivity.

It will be evident to those skilled in the art that the invention is not limited to the details of the foregoing illustrative embodiments, and that the present invention may be embodied in other specific forms without departing from the essential attributes thereof, and it is therefore desired that the present embodiments be considered in all respects as illustrative and not restrictive, reference being made to the appended claims, rather than to the foregoing description, and all changes which come with the meaning and range of equivalency of the claims are therefore intended to be embraced therein.

We claim:

1. An apparatus for measuring the refractive index of fluids, comprising a single substantially U-shaped and substantially rigid sensor rod made of a transparent material and being submersible in said fluid, the bent portion of which sensor rod has a radius of curvature at least ten and at most two hundred times larger than the radius of said sensor rod, the optimal radius of curvature for a selectable level of sensitivity being a function of a given range of indices of refraction, a housing to which are connectable the two ends of said U-shaped sensor rod, a light source inside said housing, which light source has optical access to the face of one of said sensor-rod ends, and at least one first light detector means inside said housing, which light detector means has optical access to the face of the other one of said sensor rod ends.

2. The apparatus as claimed in claim 1, wherein said optical access of said light source is constituted by a substantially straight coupling rod made of a transparent material, one end face of said coupling rod being in intimate contact with the face of one of said sensor-rod ends, and the other face of said coupling rod being in intimate contact with an end face of said light source.

3. The apparatus as claimed in claim 1, wherein said optical access of said light detector means is constituted by a substantially straight coupling rod made of a transparent material, one end face of said coupling rod being in intimate contact with the face of the other one of said sensor-rod ends, and the other end face of said coupling rod having optical access to said first light detector means.

4. The apparatus as claimed in claim 1, further comprising a second light detector means said second means being located in proximity of, and having optical access to said light source.

5. The apparatus as claimed in claim 1, wherein said light source is a light-emitting diode.

6. The apparatus as claimed in claim 1, wherein said light source is a pulsating light facilitating the filtering-out of ambient light.

7. The apparatus as claimed in claim 1, wherein said light-detecting means is a photodetector.

8. The apparatus as claimed in claim 1, wherein said housing is hermetically sealable.

* * * * *